US00PP08166P

United States Patent [19]

Moser

[11] Patent Number: Plant 8,166

[45] Date of Patent: Mar. 2, 1993

[54] HIBISCUS PLANT NAMED TANGERINE

[75] Inventor: Frank C. Moser, Alva, Fla.

[73] Assignee: Yoder Brothers, Inc., Barberton, Ohio

[21] Appl. No.: 744,075

[22] Filed: Aug. 12, 1991

[51] Int. Cl.[5] ..... A01H 5/00

[52] U.S. Cl. ..... Plt./67.8

[58] Field of Search ..... Plt./67.8, 68.1

*Primary Examiner*—James R. Feyrer

*Attorney, Agent, or Firm*—Foley & Lardner

[57] ABSTRACT

A hibiscus plant named Tangerine, particularly characterized by its orange-red flower color with a dark red eye, regular flower form, flower 11 cm in diameter, flower life of a single day, excellent pot habit, compact growth, easy to propagate, better than average resistance to bud drop, and dark green glossy foliage which is deeply lobed with serrated margins.

3 Drawing Sheets

The present invention comprises a new and distinct cultivar of hibiscus, botanically known as *Hibiscus Rosa-sinensis* L., and hereinafter referred to by the cultivar name Tangerine.

Tangerine, identified as 86-276-004 during the breeding and selection process, originated from a planned cross hybridization between two selected breeding lines in a controlled breeding program in Fort Myers, Fla. by Frank C. Moser.

The female, or seed parent is the commercial cultivar Wiesmoor Sun, about which little information is known. The pollen, or male parent is the commercial cultivar Euterpe, a light orange single with dark red eye, vigorous, upright habit, and dark green glossy foliage which is slightly lobed with a serrated margin.

Tangerine was discovered and selected as one flowering plant within the progeny of the stated cross by Frank C. Moser in August 1986, outside in ground beds in Fort Myers, Fla.

The first asexual reproduction of Tangerine was accomplished when vegetative cuttings were taken from the initial selection in October 1986 in Fort Myers, Fla., by technicians working under formulations established and supervised by Frank C. Moser.

Horticultural examination of controlled flowerings of successive generations of plants derived from cuttings taken from the original selection has shown that the unique combination of characteristics as herein disclosed for Tangerine are fixed and retained through successive generations of asexual reproduction.

Tangerine has not been observed under all possible environmental conditions. The phenotype may vary somewhat with variations in environment such as temperature, light intensity and day length, without, however, any variance in the genotype.

The following observations measurements, and comparisons describe plants that were grown in Fort Myers, Fla. in a controlled greenhouse environment and following a commercial schedule.

The following traits have been repeatedly observed and are determined to be basic characteristics of Tangerine, which, in combination, distinguish this hibiscus as a new and distinct cultivar:

1. An orange-red flower with a dark red throat from which red veins radiate outward through the petals.
2. Regular flower form, with the flower being about 11 cm in diameter.

3. Excellent pot habit, compact growth.
4. Easy to propagate.
5. Very good bud drop resistance.
6. Foliage dark green, glossy, deeply lobed and serrated.
7. Flower life of a single day.

The accompanying color photographic drawings show typical plant habit, flower and leaf characteristics of Tangerine, with colors being as true as possible with illustrations of this type.

Sheet 1 is a color photographic showing a top perspective view of Tangerine grown as a commercially finished pot plant.

Sheet 2 is a color photograph showing a close-up of the front and back of individual flowers.

Sheet 3 is a black and white photograph showing the variation in leaf shape that can characteristically be found on any one plant of Tangerine.

Of the commercial cultivars known to the inventor, the most similar in comparison to Tangerine is the male parent cultivar Euterpe.

Tangerine is similar to Euterpe in that both cultivars produce generally orange flowers with red eyes, propagate easily, and have glossy dark green attractive foliage.

Tangerine differs from Euterpe in that Tangerine has darker orange flowers with no white band between outer petals and the eye. The foliage of Tangerine is more deeply lobed than that of Euterpe. Tangerine is also more compact and more bud drop resistant than Euterpe.

In the following description color references are made to The Royal Horticultural Society Colour Chart. The color values were determined on Jul. 11, 1991. All readings were taken in an office under cool white fluorescent lights, facing a west window between the hours of 10:00 a.m. and 2:00 p.m.

Classification:

*Botanical.*—*Hibiscus Rosa-sinensis* L. cv. Tangerine.

*Commercial.*—Greenhouse pot hibiscus.

INFLORESCENCE

A. Flower (general):

*Size.*—11.0 cm.

*Borne.*—In axils of leaves, one per node.

*Form.*—Regular single.
*Life.*—One day.
*Fragrance.*—None.
*Blooming habit.*—Continuously, year round.

B. Corolla (petals):
*Texture.*—Smooth, veins slighly raised up.
*Substance.*—Rounded.
*Shape.*—Rounded.
*Color (fully open).*—Eye: Red 45A. Throat: Red 47C. Body: Interveinal: Red 33A. Main veins: Red 45A (initiating from throat).

C. Bud (one day prior to opening:
*Size.*—5.5 cm.
*Shape.*—Cigar shaped.
*Color.*—Interveinal: Red 44A. Main veins: Red 45A.

D. Calyx: Cup shaped, 5 pointed lobes, a single prominent midvein per lobe, membranous.
*Length.*—2.5 cm.
*Color.*—Green 137B.

E. Epicalyx: 5 pointed, narrow, sword-shaped bracts.
*Length.*—1.3-2.0 cm.
*Color.*—Green 137A.

F. Peduncle:
*Length.*—3.0-4.0 cm.
*Strength.*—Medium to strong.
*Aspect.*—Smooth.
*Color.*—Greyed-purple 183B interspersed with yellow-green 144A.

G. Reproductive organs:
*Androecium (stamens).*—Anthers: Numerous. Filaments: Pink, 4 mm in length. Pollen: Abundant. Color: Yellow 15A. Staminal column: Upper 33% antheriferous. Length: 7.5 cm. Color: Red 48B.
*Gynoecium (pistil).*—Stigma: 5 in number, rounded, discoid, hairy. Diameter: 2.0 mm. Color: Red 46A. Style: Length: 8.0 cm. Color: Yellow 2D. Branches: 5 in number. Length: 3 mm. Color: Red 45C. Ovary: Bell-shaped. Color: Green 144D.

PLANT CHARACTERISTICS

A. Foliage:
*Arrangement.*—Alternate.
*Shape.*—Juvenile: Ovate, cordate, lobed, serrated margin. Mature: Ovate, cordate, lobed, serrated margin. Color: Dark Green 147A.
*Petiole.*—Length: 3.5-5.5 cm. Aspect: Smooth. Color: Greyed-purple 183A interspersed with yellow-green 144A. Stipules: Two per node, shape acicular (needle shaped). Color: Greyed-purple 183A interspersed with yellow-green 144A.

B. Stem: Aspect smooth, becoming woody with age.
C. Plant habit: Excellent, compact.
D. Breaking action: Average.
E. Rooting: Excellent.
F. Growth regulator: Required.
G. Low light bud initiation: Good.
H. Shipping tolerance: Very good.

I claim:

1. A new and distinct cultivar of hibiscus named Tangerine, as shown and described and illustrated.

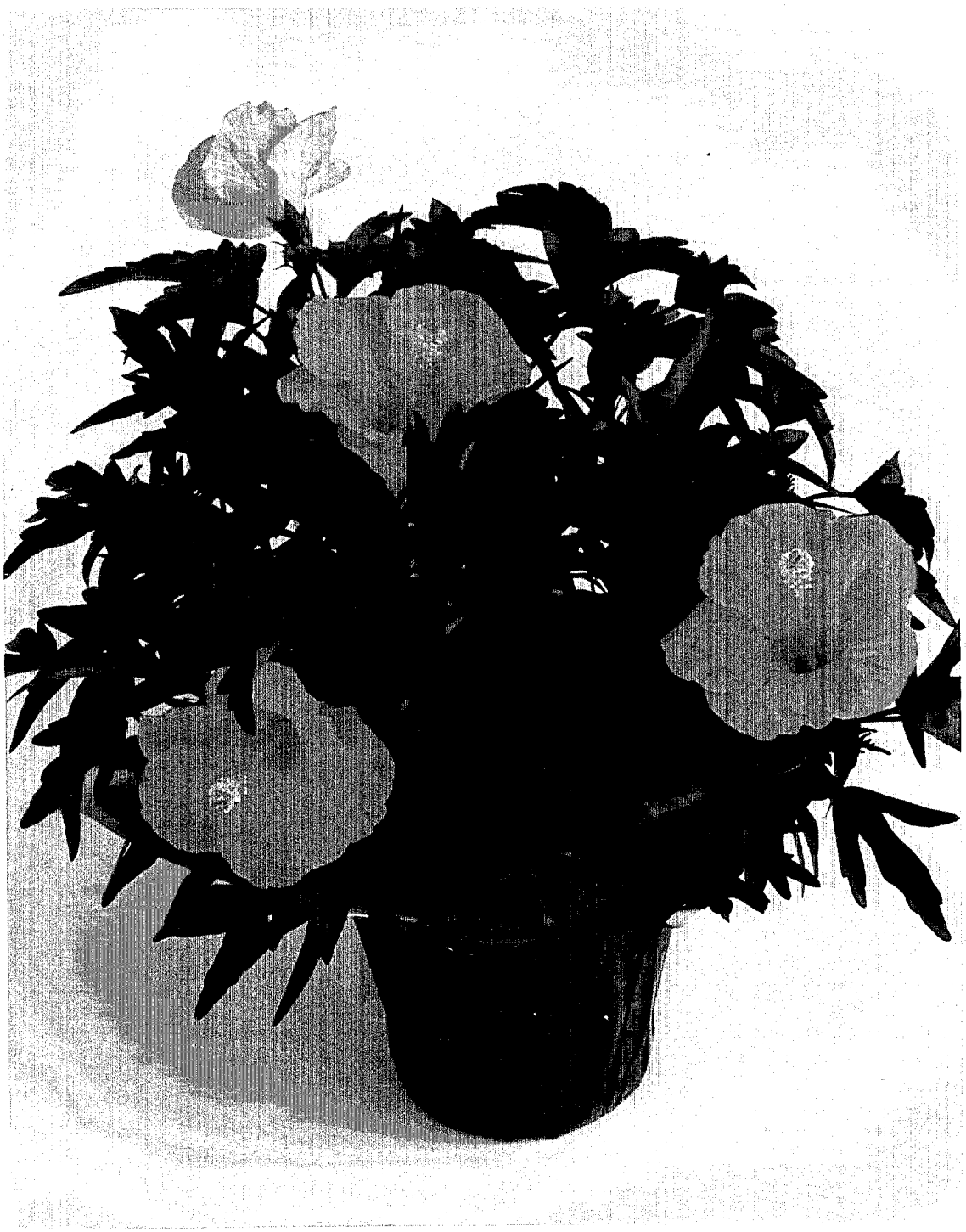

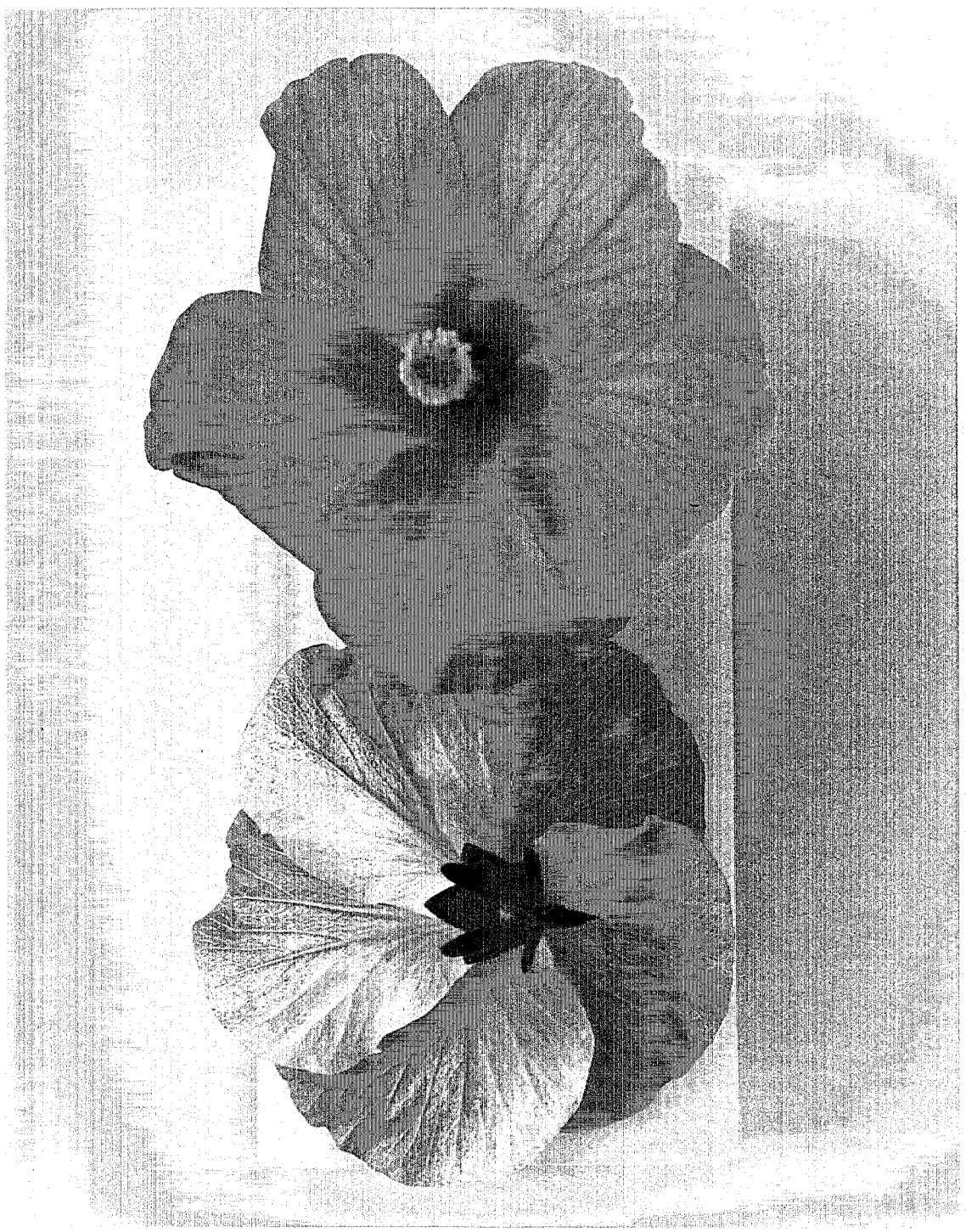

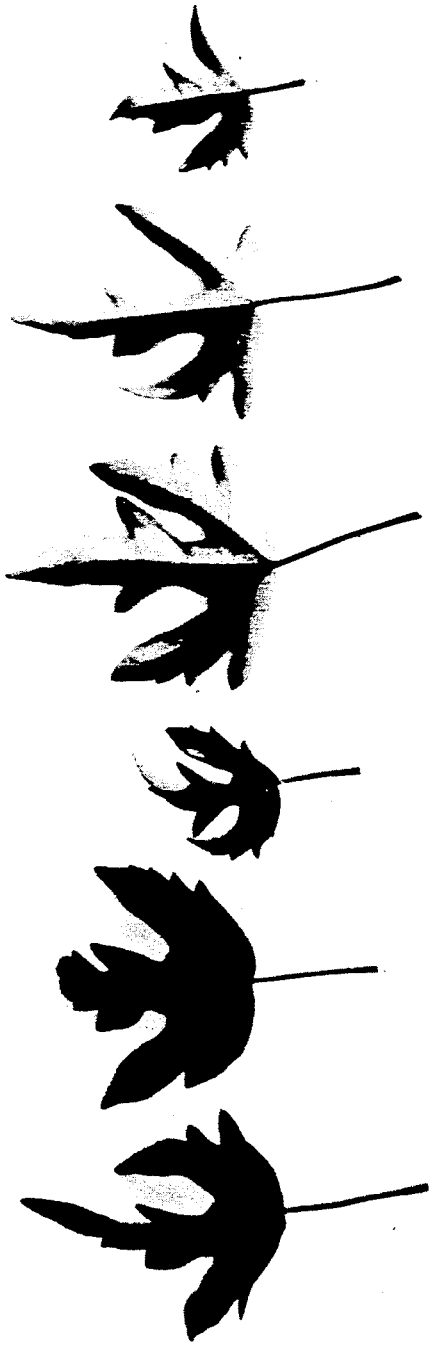

* * * * *